(12) United States Patent
Fehr

(10) Patent No.: US 9,822,638 B2
(45) Date of Patent: Nov. 21, 2017

(54) IN-SITU ROCK TESTING TOOL

(71) Applicant: 1464684 Alberta Limited, Calgary (CA)

(72) Inventor: Cory Fehr, Chestermere (CA)

(73) Assignee: 1464684 Alberta Ltd., Chestermere (CA)

( * ) Notice: Subject to any disclaimer, the term of this patent is extended or adjusted under 35 U.S.C. 154(b) by 672 days.

(21) Appl. No.: 14/473,641

(22) Filed: Aug. 29, 2014

(65) Prior Publication Data
US 2015/0136388 A1 May 21, 2015

Related U.S. Application Data

(60) Provisional application No. 61/884,196, filed on Sep. 30, 2013.

(51) Int. Cl.
| | |
|---|---|
| *E21B 49/00* | (2006.01) |
| *E21B 33/128* | (2006.01) |
| *E21B 36/00* | (2006.01) |
| *E21B 43/26* | (2006.01) |
| *E21B 33/127* | (2006.01) |
| *G01N 33/24* | (2006.01) |

(52) U.S. Cl.
CPC .......... *E21B 49/00* (2013.01); *E21B 33/1277* (2013.01); *E21B 33/1285* (2013.01); *E21B 36/005* (2013.01); *E21B 43/26* (2013.01); *G01N 33/24* (2013.01)

(58) Field of Classification Search
CPC .. E21B 33/1285; E21B 33/128; E21B 36/005; E21B 43/26; E21B 36/00; G01N 33/24; G01N 3/24; G01N 3/00; G01N 3/10; E02D 1/00; E02D 1/02; E02D 1/022
See application file for complete search history.

(56) References Cited

U.S. PATENT DOCUMENTS

| | | | |
|---|---|---|---|
| 3,175,392 A | 3/1965 | Tharalson | |
| 3,349,610 A | 10/1967 | Noel | |
| 3,427,871 A | 2/1969 | Handy | |
| 3,499,320 A | 3/1970 | Fox | |

(Continued)

OTHER PUBLICATIONS

Carlton A. Hay, Developmnet of an Insitu Rock Shear Testing Device, 2007.*

(Continued)

*Primary Examiner* — Wei Wang
(74) *Attorney, Agent, or Firm* — Michael A. Bondi; Moss & Barnett

(57) ABSTRACT

A shear tester for in-situ determination of rock formation geomechanical properties is provided. The tester has a radially expandable cylindrical membrane, a metal sheath covering at least a portion of the outer surface of the membrane, at least one stud fixed on the sheath, at least one cone fixed on each of the at least one stud, and a piston operable to apply an upward axial force on the metal sheath. A device for the same use comprises the shear tester and a pressuremeter. A method of using the shear tester comprises applying a normal force to the formation by expanding the membrane until at least one of the at least one cone penetrates the rock formation and applying an upward axial force to the at least one of the at least one cone by operating the piston until at least a portion of the rock formation shears.

19 Claims, 7 Drawing Sheets

(56) References Cited

U.S. PATENT DOCUMENTS

| | | | |
|---|---|---|---|
| 3,562,916 A | 2/1971 | Duckworth |
| 3,610,035 A | 10/1971 | Handy |
| 3,673,861 A | 7/1972 | Handy |
| 3,785,200 A | 1/1974 | Handy |
| 4,075,885 A | 2/1978 | Handy |
| 4,539,851 A | 9/1985 | Lutenegger |
| 4,557,147 A | 12/1985 | Rohde |
| 4,773,259 A | 9/1988 | Handy |
| 5,540,101 A | 7/1996 | Capelle |
| 5,585,555 A | 12/1996 | McRae |
| 8,141,419 B2 | 3/2012 | Tchakarov |

OTHER PUBLICATIONS

Ballouz, ISST : In-Situ Shear Test for Soil Investigations, JLG—Journees Libanaises de Geotechniques, 2002.
Bechtum, Automation and further development of the borehole shear test, Iowa State University Digital Repository @ Iowa State University, 2012.
Using pressuremeters, Cambridge Institu Ltd, 2012.
Failmezger, Measurement of effective stress shear strength of rock, 2008.
Hay, Development of an Insitu Rock Shear Testing Device, Dissertation for University of Florida, 2007.
Taheri, Study on Shear Strength and Deformability Properties of Rock Masses by In-situ and Laboratory Testing Methods, 2013.

\* cited by examiner

IN-SITU ROCK TESTING TOOL

FIELD OF THE INVENTION

This invention is in the field of rock testing tools, and more specifically to such tools that can be used to determine in-situ rock formation geomechanical properties.

BACKGROUND

To determine the strength of a rock formation and its capabilities in containing pressure, several geomechanical parameters must be known. These parameters include but are not limited to: Young's modulus, which is a measure of the stiffness of an elastic material, cohesion, the component of rock shear strength that is independent of inter-particle friction, Poisson's ratio, which represents the negative ratio of transverse to axial strain, and minimum in-situ stress, which is the amount of pressure it takes to initiate the opening of an existing fracture. The conventional method of obtaining these values is to perform a mini-frac and to test core samples at an offsite lab. However, these procedures are very costly and take a very long time. Furthermore, core samples are inherently disturbed during the coring process and thus may not accurately represent the in-situ rock conditions.

There have thus been various instruments developed for testing geomechanical properties of in-situ rock formations. For example, pressuremeters are sometimes used to determine minimum in-situ stress and borehole shear testers are sometimes used to test rock shear strength.

However, conventional pressuremeter tools are generally unable to provide reliable minimum in-situ stress values due to the difficulty in pinpointing the initial onset of a crack in a formation. Also, while conventional pressuremeters can determine many geomechanical strength properties, they cannot provide sufficient data to determine cohesion. Conventional pressuremeters are similarly unable to determine permeability (the measure of a rock's ability to transmit fluids) due to the need to inject fluid or gas into a rock, which conventional pressuremeters cannot do. Presently-available self-boring pressuremeters allow for fluid movement through the tool itself, but cannot exert the force required for all sought-after testing functionality, both on the injection and cavity expansion aspects of their testing.

Borehole shear testers are another instrument that can be used in testing geomechanical properties. They are typically one dimensional tools that can provide only partial answers to the questions surrounding geomechanical behavior. For the most part, they are limited in their normal force exertion capability, functioning generally in soft soil only. Conventional borehole shear testers are also rigid in their design and occupy the entire wellbore when deployed.

Presently-available in-situ rock testing equipment thus does not provide comprehensive information regarding formation characteristics. As a further example, thermal hardening of a material is a response which can help increase that material's resistance to failure and conventional means of testing for the effects of thermal hardening involve high temperature tri-axial testing, which is currently unavailable using presently-available in-situ tools and methods.

SUMMARY OF THE INVENTION

It would be advantageous to have an efficient, cost effective in-situ tool and method that can provide a wide range of accurate information regarding rock formation characteristics.

In an aspect, a shear tester for in-situ determination of rock formation geomechanical properties comprises a radially expandable cylindrical membrane, a metal sheath covering at least a portion of the outer surface of the expandable membrane, at least one stud fixed on the outer surface of the sheath, at least one cone fixed on each of the at least one stud, and a piston operable to apply an upward axial force on the metal sheath.

In a further aspect, a device for in-situ determination of rock formation geomechanical properties comprises a pressuremeter, and a shear tester comprising a radially expandable cylindrical membrane, a metal sheath covering at least a portion of the outer surface of the expandable membrane, at least one stud fixed on the outer surface of the sheath, at least one cone fixed on each of the at least one stud, and a piston operable to apply an upward axial force on the metal sheath.

In yet a further aspect, a method for in-situ determination of geomechanical properties of a rock formation comprises the steps of providing a shear tester comprising an expandable membrane, a metal sheath covering at least a portion of the expandable membrane, at least one stud fixed on the surface of the sheath, at least one cone fixed on each of the at least one stud, and a piston operable to apply an upward axial force on the metal sheath, applying a normal force to the formation by expanding the membrane until at least one of the at least one cone penetrates the rock formation, and applying an upward axial force to the at least one of the at least one cone by operating the piston until at least a portion of the rock formation shears.

The shear tester and the device and method that use the shear tester can be used in-situ to determine or calculate information regarding rock formation characteristics, including normal stress, shear stress, and fracture closure pressure.

DESCRIPTION OF THE DRAWINGS

While the invention is claimed in the concluding portions hereof, aspects of the invention are provided in the accompanying detailed description which may be best understood in conjunction with the accompanying diagrams where like parts in each of the several diagrams are labeled with like numbers, and where:

DETAILED DESCRIPTION OF THE ILLUSTRATED EMBODIMENTS

A rock testing tool that can be used in-situ to determine rock geomechanical properties is provided.

Figure 1:
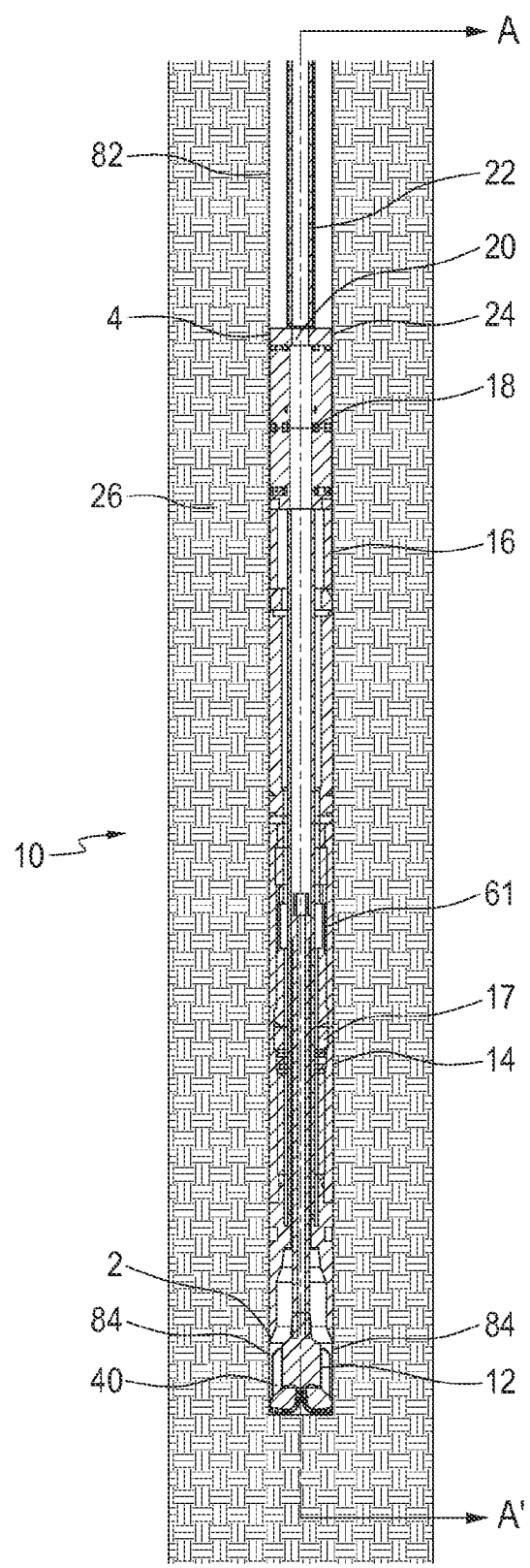
FIG. 1 is an elevational view of an in-situ rock testing tool in an aspect, shown mounted within a test socket.
Figure 2:
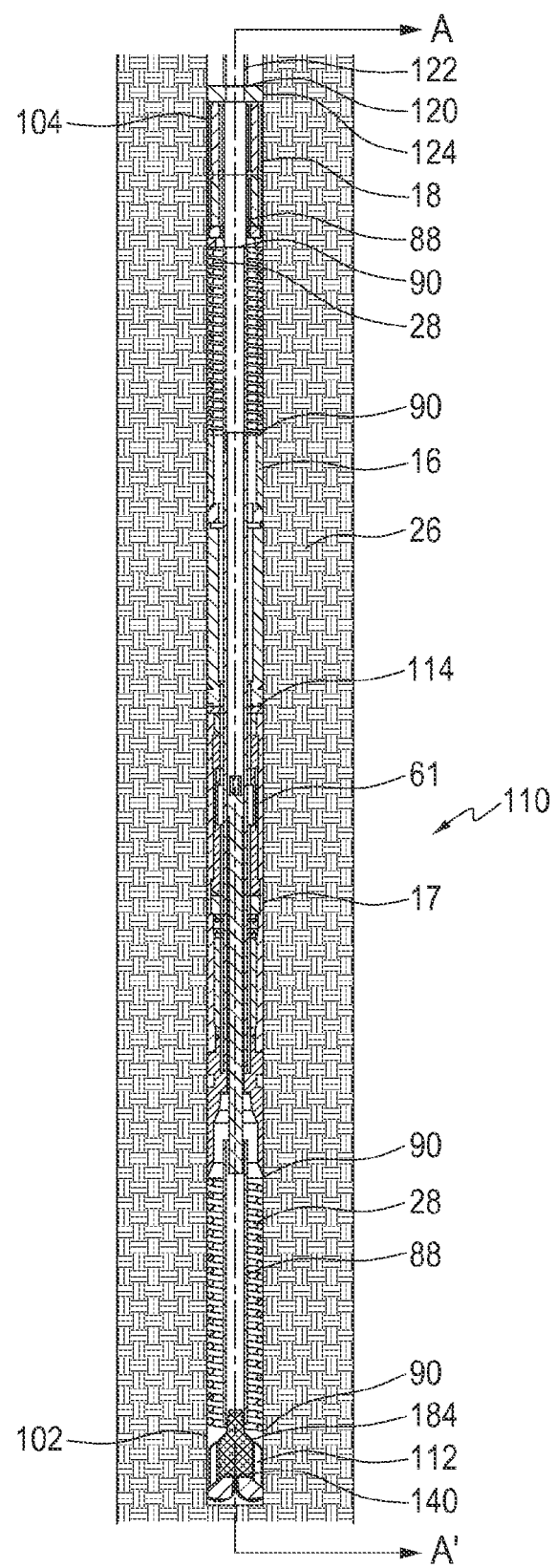
FIG. 2 is an elevational view of in-situ rock testing tool in a further aspect, again shown mounted within a test socket.

FIGS. 1 and 2 illustrate rock testing tools 10, 110, respectively, in aspects deployed in a vertical well bore within a test socket 82.

The tools 10, 110 comprise a body 24, 124 of generally elongate cylindrical form extending along a central axis from A-A' between a first end 2, 102 and an opposing second end 4, 104 situated at a spaced distance apart along the axis A-A'. Central axis A-A' could run in any direction, including substantially horizontal or vertical directions, though in the aspects shown, runs substantially vertically. Along the axial direction of the body 24, 124, testing tools 10, 110 can comprise a high pressure pressuremeter 14, 114 as well as a shear head 18. In some aspects, the pressuremeters 14, 114 could be self-boring, though in other aspects the pressuremeters 14, 114 may be pushed-in pressuremeters that are forced into the ground to raise the state of stress in the surrounding formation 26 or could be placed in a pre-bored pocket. The tools 10, 110 in FIGS. 1 and 2 also comprise a micro/mini-frac tester 61.

The tool 110 shown in FIG. 2 additionally includes high temperature heating coils 28 of an in-situ heating mechanism.

The bodies 24, 124 may be assembled together from initially separate components, for example by threaded mating of different components such as the pressuremeter 14, 114 and shear head 18. In some aspects, however, the bodies 24, 124 could be manufactured in a single integrated tool having sections operative to provide the required functionality of a pressuremeter, micro-frac tester, and shear head.

In some aspects, an axial bore or center tube 22, 122 may pass through each of the pressuremeter 14, 114 and shear head 18 along axis A-A' to accommodate reaching of a drill rod string 20, 120 into the body 24, 124 at the second end 4, 104 thereof from a suitable drive arrangement at the surface of the test socket 82. The tool body 24, 124 can be operatively attached to the drill rod string 20, 120, which acts as a pull rod for use in axially displacing the body 24, 124 within the test socket 82 when the shear head 18 is activated. However, in other aspects, such as that shown in FIG. 6, the center tube 222 runs axially only through an upper portion of the tool body 224, as a drill rod string is not required to run through the body 224 since the axial force required to displace the body 224 may be provided by other means, namely, by a piston 235 supplying a force upward on the shear tester 218.

The Shear Head

Figure 3:
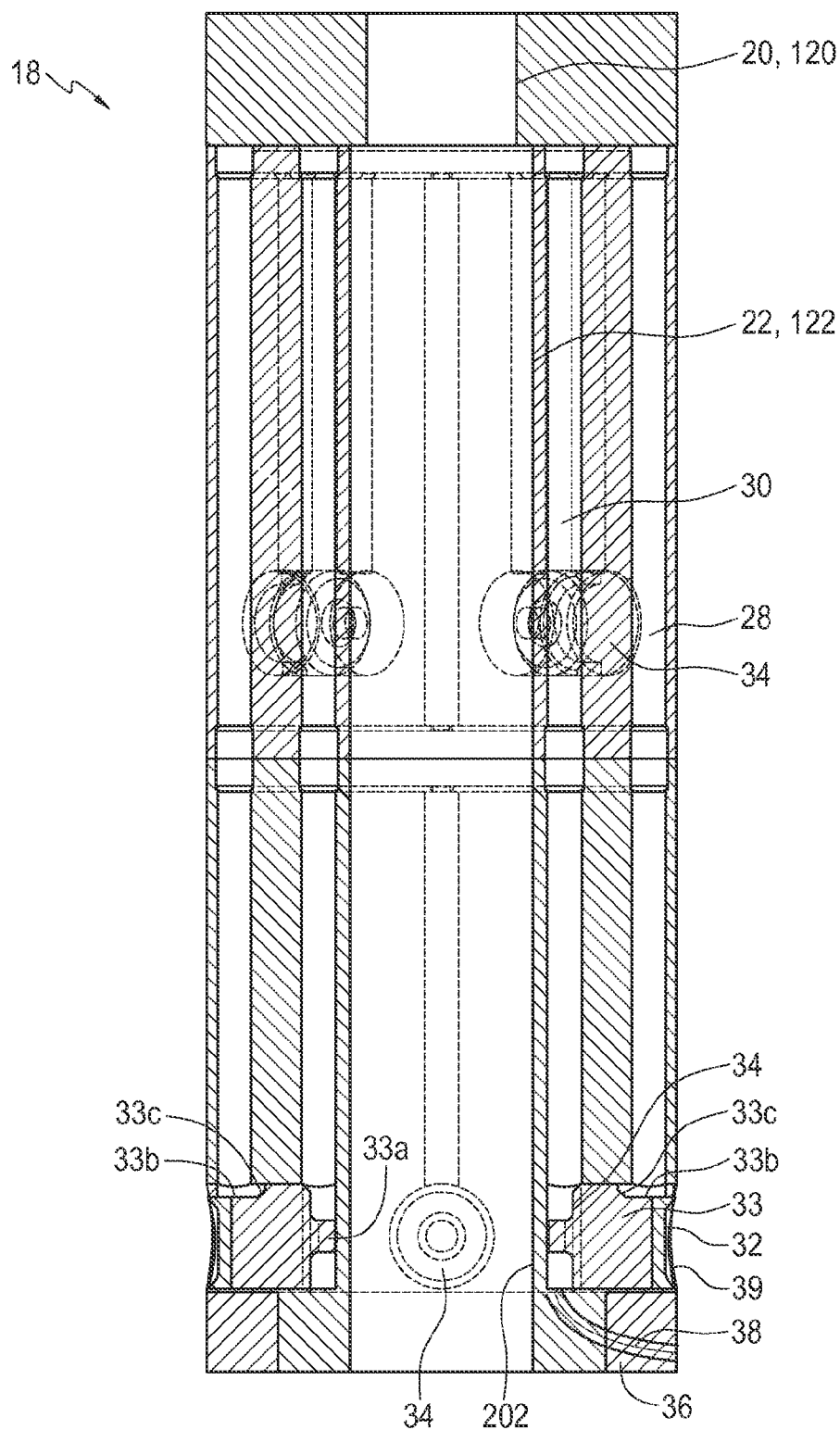
FIG. 3 is a cross-sectional side elevation view of a shear head unit of the tools of FIGS. 1 and 2.

The shear head 18 of FIGS. 1 and 2 is shown in further detail in FIG. 3. In the aspect shown, the shear head 18 comprises eight pistons 33, each of which comprises a piston head 34 slidably disposed in a respective radial port that provides a channel in the body 24, 124 of the tool 10, 110 between the outside surface of the body 24, 124 to the central tubing 22. The eight pistons 33 are divided into two sets of four, each set being disposed at a respective position spaced along the axis A-A' from the other set. Within each set, the four pistons 33 are equally spaced apart from one another on a plane in a circumferential path around the central axis A-A', thus lying in their respective radial ports at ninety degree increments around the central tubing 22. The positioning of the four pistons 33 in one set is offset by forty-five degrees from the other set, whereby the eight total pistons 33 are equally distributed around the central tubing 22 and the central axis A-A' therein at equal forty-five degree intervals.

For each of the eight radial ports, a respective pair of channels 28, 30 extend into the port from the topside thereof on opposite sides of a fluid-tight seal between the respective piston 33 and the wall of the port. The channels 28, 30 could comprise axial bores machined into the tool body 24, 124 to form integrally defined fluid pathways through which pressurized fluid is conveyed in order to radially displace the piston 33 in respective directions back and forth in its respective radial port.

The pistons 33 shown in FIG. 3 are in a refracted position in which a reduced-diameter end 33a of the piston 33 abuts against the physical barrier 202 that separates the interior of the central tubing 22 from the radial port. This reduced-diameter end 33a of the piston 33 is smaller than the port diameter, thus leaving an open space between the remainder of the piston 33 and the inner end of the port around the circumference of the reduced-diameter end 33a of the piston 33. Located across the seal between the reduced-diameter end 33a of the piston 33 body and the port wall is a topside cutaway 33b in the piston 33. A radially innermost end 33c of the cutaway 33b thereof nearest the central axis A-A' creates a radially-outward facing shoulder between the cutaway and the full-diameter portion of the piston 33 that seals with the port wall. The open end of the port 39 at the circumferential surface of the tool body 24, 124 is sized and shaped to prevent full deployment of the piston 33 therefrom. A bevel between the bottom of the cutaway 33b and the end face 33c thereof forms a stop feature that engages an inward facing surface at the top of the port opening 39 to prevent full separation of the piston 33 from the body 24, 124. A shear plate 32 is connected to the outer end of the piston 33 that lies opposite to the reduced diameter inner end 33a thereof. In the normal retracted state of the piston 33, the entire piston 33 and the shear plate 32 are situated inside the body 24, 124 so as not to project radially beyond the circumferential surface thereof.

The channel 30 located nearest the central axis A-A' is disposed on the side of the piston seal nearest the center tube 22 and forms an expansion or extension channel, as conveyance of pressurized fluid into this channel can exert pressure on the inward facing end of the full-diameter portion of the piston 33 at the annular surface thereof that encircles the reduced-diameter end 33a of the piston 33. This forces the piston 33 radially outwardly into an extended state reaching radially outwardly beyond the circumferential surface of the body 24, 124. This extension of the piston 33 forces the respective shear plate 32 out of the port opening 39 and against the bore wall of the test socket 82.

The other channel 28 located furthest from the central axis A-A' is disposed on the side of the piston seal nearest the outer circumference of the body 24, 124 and forms a contracting or retraction channel, as conveyance of pressurized fluid into this channel 28 will exert pressure on the outward facing end of the full-diameter portion of the piston 33 at the inner end 33c of the cutaway 33b, thus forcing the piston 33 and attached shear plate 32 radially inwardly back into the fully retracted state inside the body 24, 124. The beveled end of the cutaway 33b ensures an open space remains between the inside surface of the body's 24, 124 outer wall and the upright end face 33c of the cutaway 33b when the piston 33 is extended so as to provide a suitable surface area for the fluid of the retraction channel 28 to act on in the radially inward direction toward the central axis A-A'.

In some aspects, the channels 28, 30 may feature suitable hydraulic fittings at upper ends thereof at the top end of the shear head 18, from which hydraulic lines extend up to the surface for connection to a suitable source for providing pressurized fluid to these channels 28, 30.

The configuration of the shear head 18 can be engineered to be compatible with a high pressure pressuremeter. For example, the shear head 18 can be robust, exerting normal forces in excess of 10,000 KPa. In some aspects, the shear head 18 is engineered to fit around the hollow center tube 22, 122 so as to be compatible with a self-boring pressuremeter 14, 114. However, it is understood that in some aspects, the pressuremeter may not be self-boring and there may be no center tube 22, 122 present or required.

Figure 6:
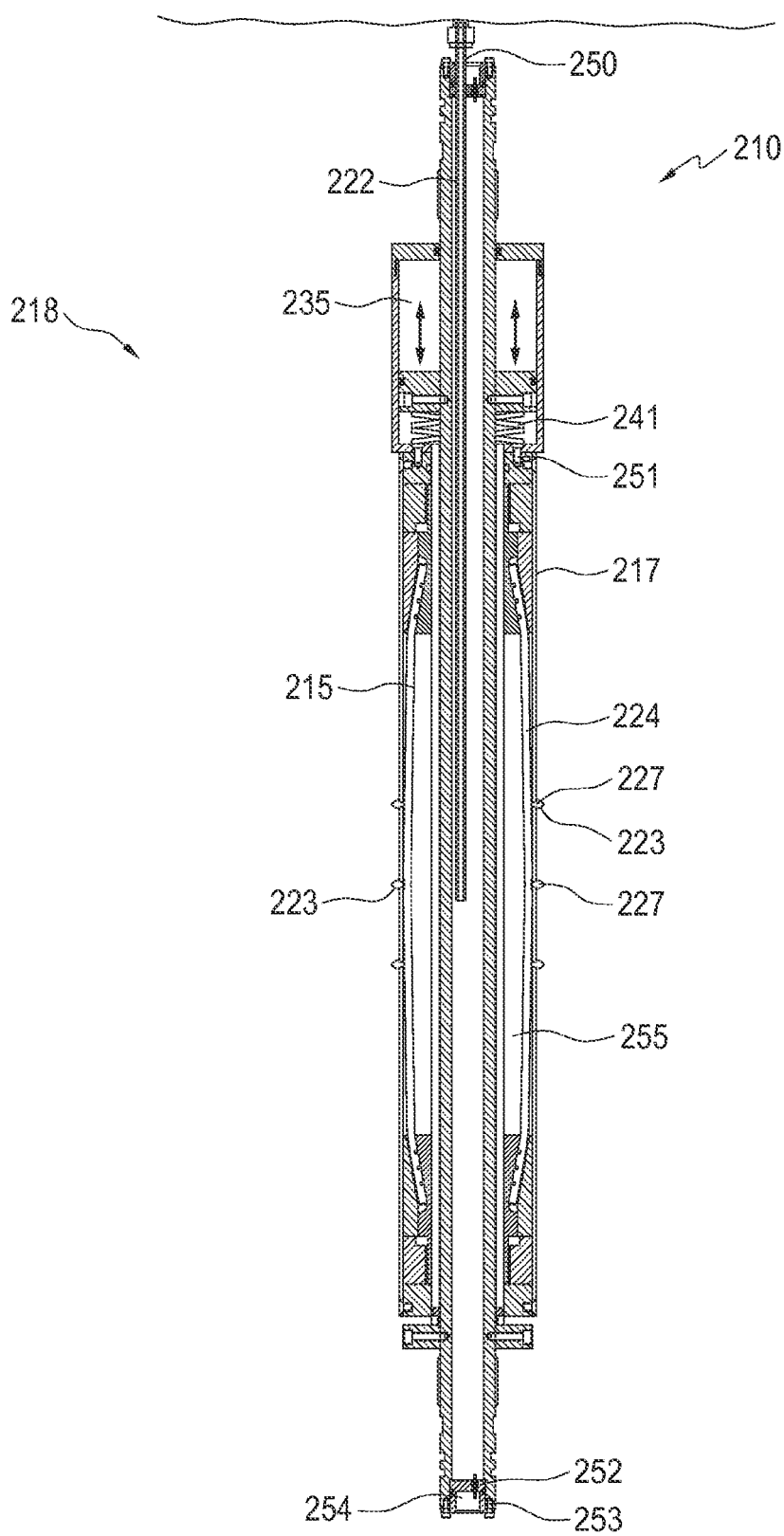
FIG. 6 is a cross-sectional side elevation cutaway view of an in-situ rock testing tool in yet a further aspect.

In the aspect shown in FIG. 6, channels 28, 30 are not required as pistons 33 are not present. The center tube 222 runs axially only through an upper portion of the tool body 224, with hydraulic lines able to transmit pressure to the lower half of the tool 210.

The shear head 218 of the aspect shown in FIG. 6 lacks shear plates 32 shown in the aspect of FIG. 3. Instead, the shear head 218 comprises two moveable sections 215, 235. The first moveable section is a radially expandable membrane or dilatometer 215 covered and protected by a metal sheath or Chinese Lantern (otherwise known as a CHL) 217. The metal sheath 217 could be made out of steel and membrane 215 can be pneumatically inflated. In some aspects, the sheath 217 can measure external fluid pressure. The second moveable section is a piston 235 that can move in the axial direction and supplies the shear force to the shear head 218.

The membrane 215 and sheath 217 can be of fixed length, with one end slidable with respect to the other end. The membrane 215 could be manufactured out of, for example, continuous layers of Kevlar™ so as to allow the membrane 215 to expand radially, while its axial length decreases and it maintains a constant thickness.

The membrane 215 can engage with the test socket 82 through studs 223 fixed on the outer surface of the protective sheath 217. Each stud 223 can carry a sharp point or cone 227 on its tip. The known cross-sectional area of the stud 223 may be used to derive the available normal force, while the cross-sectional area of the piston 235 may be used to calculate the shearing force. The extent to which the cone 227 penetrates the ground upon expansion of the membrane 215 can be assumed or calculated, and from this penetration depth and angle of the cone 227, one can derive the shearing area and normal area when shearing. Since the normal and shear forces are known, the normal stress and shear stress can then be calculated.

A biasing means, such as a spring 241, may be provided that biases the membrane 215 into a retracted position against the body 224 of the tool 210. In other aspects, the biasing means may be provided by the inherent spring action of the metal sheath 217. The membrane 215 might otherwise float freely axially along the body 224 of the tester 210.

The Pressuremeter

Figure 4:
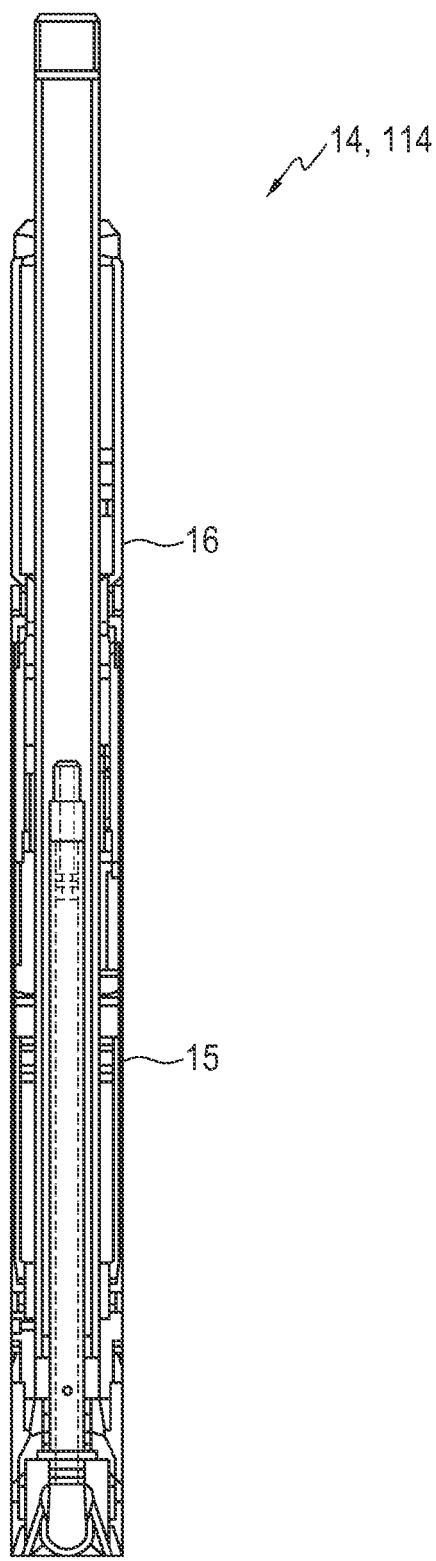
FIG. 4 is a cross-sectional side elevation view of a pressuremeter unit of the tools of FIGS. 1 and 2.

The pressuremeter section 14 of the tool 10 shown in FIG. 1 defines the lower end 2 of the body 24, since the tool 10 in FIG. 1 lacks the additional heating mechanism or coils 28 of the tool 110 shown in FIG. 2. The pressuremeters 14, 114 are shown in further detail in FIG. 4.

A coupling 16 may be disposed above the pressuremeter section 14, 114 of the tool body 24, 124 and can feature suitable high-pressure fittings for connection of high pressure gas or hydraulic lines thereto. These gas and hydraulic lines may form one or more inlets for feeding pressurized gas or hydraulic fluid into a high pressure flexible membrane 15 of the pressuremeter 14, 114 from a suitable source at the surface. Through the high pressure inflation line coupling 16, the high pressure flexible membrane 15 can be expanded radially outward beyond the cylindrical outer peripheral surface of the body 24, 124 such that it abuts the generally cylindrical wall of the test socket borehole 82. In some aspects, the pressuremeter 14, 114 can apply load forces of up to five times higher than conventional equipment to the test socket 82 walls. In some aspects, the high pressure fittings and high pressure membrane 15 can safely attain notably higher pressures than conventional self-boring pressuremeters, for example, in the order of 30,000 KPa.

The Heating Mechanism

The tool 10 of FIG. 1 comprises the pressuremeter 14 and shear head configuration 18. FIG. 2 also comprises the pressuremeter 114 and shear head configuration 18 and additionally comprises a heating mechanism 28, which, in the aspect shown in FIG. 2 comprises at least two separate heating coils 28 that can heat the formation 26 surrounding the test socket 82, for example to 150 degrees Celsius. The heating coils 28 may be electrical resistance heating coils, for example powered via power cables 88 routed through the tool 110 from a suitable power source at the surface. However, other configurations may also be possible, for example using heat exchange coils through which heated fluid is circulated from a suitable source. The illustrated coils 28 encircle the central tubing 122 a short distance outward therefrom so as to lie beneath the circumferential surface of the body 124 in close proximity thereto. Heat energy from the coils 28 can thus be emitted outwardly from the body 124 in which the coils 28 are disposed. At least one insulative barrier 90 can isolate the thermal elements 28 from the rest of the tool 110.

The Micro-Frac Tester

Figure 7A:
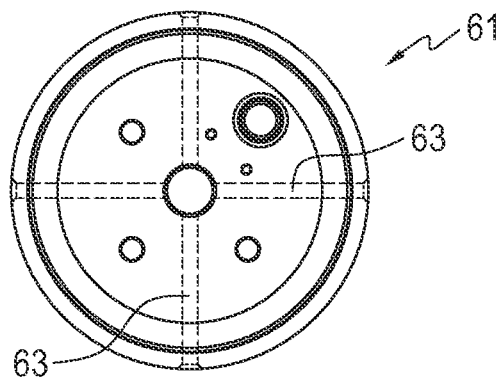
FIG. 7a is a cross-sectional view of a micro-frac tester.
Figure 7B:
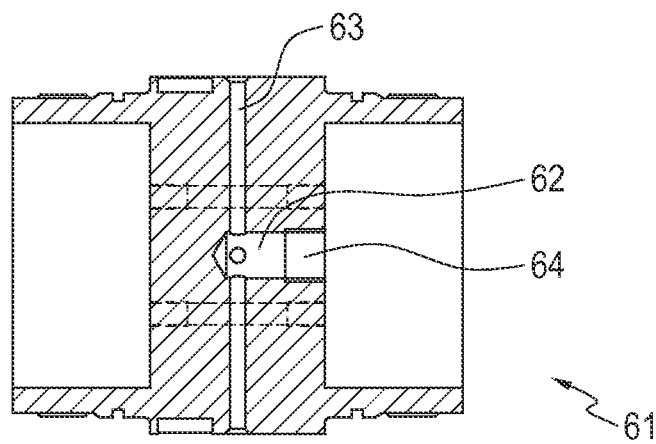
FIG. 7b is a cross-sectional side elevation cutaway view of the micro-frac tester shown in FIG. 7a taken along cutaway lines B-B'.

In the aspects shown in FIGS. 1 and 2, a mini- or micro-frac tester 61 comprises a series of injection ports 63 which are shown in more detail in FIGS. 7a and 7b. Corresponding valves 62 and pressure cells 64 can be used to control the flow of fluid and take pressure readings, respectively. The mini-frac tester 61 can allow for the determination of how much force would be required to re-open a newly created fracture in a formation 26. In some aspects, the pressure cells 64 have a 60,000 psi pressure capacity and a +/−0.2% accuracy with resolution to 1 psi. Readouts of what the pressure cells 64 are monitoring can be displayed at the surface using appropriate cables running downhole.

In Operation

In operation, the tool 10, 110 is advanced into a test socket 82 drilled into the formation 26. The test socket 82 may be drilled by the tool 10, 110 using its own drill bit 12, 112 in conjunction with axial and percussive forces from a drilling rig and hammer adapter to which it may be attached.

In the aspects shown, a drill bit 12, 112 is disposed on the lower end of the drill rod string 20, 120 so that the cutting edges of the drill bit 12, 112 are disposed outside of the body 24, 124 just a short axial distance beyond the lower end 2, 102 thereof. Through driven rotation of the drill rod string 20, 120, the tools 10, 110 can bore their own test sockets 82 to a desired depth from the surface, during which the length of rod string 20, 120 can be increased as needed by unwinding of additional lengths of continuous drill rod 20, 120 off of a spool or the like, or by adding additional discrete sections to a string of thread-together drill rod sections.

The drill bits 12, 112 could be toothed drill bits comprising tungsten carbide PDC and may be accompanied by a cutting shoe 40, 140 disposed at the lower end 102 of the body 24, 124 which may be manufactured out of tungsten carbide. An axial and percussive force provided by a drilling rig and hammer adapter is transmitted through the body 24, 124 of the tool 10, 110 and into the cutting shoe edge 40, 140 which can aid the drill bits 12, 112 with boring of the test socket 82. A combined drill bit 12, 112 and cutting shoe 40, 140 assembly of this type may be commercially available, such as the Cambridge Self-Boring Pressuremeter™ from Cambridge In-situ.

A hollow drill string 20, 120 may be used, whereby the drill string 20, 120 defines a central conduit passing through it from the surface to allow pumping of drilling fluid downhole and into the drill bit 12, 112. A center tubing string 22, 122 can be disposed annularly around the drill string 20, 120 radially outward therefrom so as to leave an annular space between the two. The center tubing 22, 122 can run from the surface into the upper end 4, 104 of the tool body 24, 124, and further onward through the internal axial passage thereof before stopping short of the drill bit 12, 112. During the drilling operation, drilling fluid is circulated through the drill string 20, 120 to the drill bit 12, 112 and then back up to surface through the annular space created between the drill string 20, 120 and the center tube 22, 122.

Once the device 10, 110 is advanced to a first desired test depth, low pressure fluid injection through the drill bit 12, 112 via the hollow drill string 20, 120 begins in order to accumulate a fluid column in the borehole of the test socket 82. By pressurizing the fluid column and recording the flow rates required to obtain various steps in that pressure, a linear trend can be established. This linear trend is a function of the permeability and shape factor.

However, as mentioned, the tool may not be self-boring in some aspects, and could be pushed in to the formation 26 or placed in a pre-bored hole or socket 82. In such aspects, the tool may not comprise the drill bit 12, 112 or the drill rod string 20, 120, or other features required for the tool to be self-boring. Instead, the tool could be advanced into the pre-bored socket 82 or pushed in to the formation 26 without the tool itself boring a hole, and could proceed with operation of the pressuremeter, shear head, and/or the micro-frac tester.

Operation of the Pressuremeter

The pressuremeter 14, 114 can operate a series of tests in which pressure is applied to and then removed from the bore wall of the test socket 82 by the radial lateral expansion and collapse of the pressuremeter's 14, 114 flexible membrane 15 out from and back into the tool body 24, 124. During this process, the cavity walls of the socket 82 can be displaced.

Once the cavity walls have been physically affected by the expansion and contraction of the flexible membrane 15, fluid can be injected into the formation 26 via a separate source at surface. In some aspects, the fluid can be injected through to the drill bit 12, 112, though in other aspects where the pressuremeter is not self-boring, the fluid can be injected directly through valves and bores machined into the body of the pressuremeter and into the formation 26.

This injection can induce fracturing of the formation 26. By monitoring the behavior and response of the downhole pressure via bottom hole pressure cells and a sending unit 84, 184 at or proximate the bottom end 2, 102 of the body 24, 124 and separate surface equipment receiving the signals from the pressure cells and sending unit 84, 184 during fracture initiation, breakdown, propagation, shut-in, and closure, minimum horizontal stress can be determined. In some aspects, the sending unit 84, 184 can employ electrical cabling to convey signals to receiver equipment at the surface. Once this process has finished, the high pressure flexible membrane 15 will deflate and the shear head 18 will activate.

Combining injection pressure readings of the micro-frac fluid with cavity expansion and contraction equations can result in the in-situ determination of multiple geomechanical properties including shear modulus, Young's modulus, minimum horizontal stress, limit pressure, cohesion, friction angle, etc.

Operation of the Shear Head

To calculate direct shear of a rock formation, a shear head 18, 218 can be used to apply a normal force to the test socket 82, while an increasing force is applied at right angles until the material of the socket 82 shears. An axial movement detector can detect the point of material shear, and combined with the known co-ordinates of the normal and shear stress can allow the internal angle of friction and/or the cohesion to be determined.

To initiate a shear test, expansion channel 30 of the shear head 18 shown in FIG. 3 will become pressurized, for example to 12,000 KPa, pushing hydraulic fluid against the piston head 34 and subsequently advancing the piston 33. Shear plates 32 connected to the piston 33 will apply a normal force, for example of 12,000 KPa, to the wall of the test socket 82. An axial pulling force, for example of 5,000 KPa, will then be applied to the tool 10, 110 by slow lifting of the drill string 20, 120 by the drilling rig while the shear plates 32 are engaged to the bore wall of the test socket 82. Shear force can be measured by hydraulic load cells 36 and the response sent to surface equipment via feedback lines 38 that run up through the tool body 24, 124 and onward up the central tubing 22, 122 to the surface. As the shear plates 32 respond to rock grain dilation or compaction as the shear forces act on the formation 26, their position can be held constant by automatic pressure adjustments in the expansion 30 and contraction channels 28. This functionality enables a consistent shear plate position while allowing the normal stress to vary. Once shear has been achieved, the shear plates 32 can then be refracted via hydraulic pressurization of the contraction channel 28 and depressurization of the expansion channel 30, which can apply force and vacuum to the opposite sides of the piston head 34 simultaneously, thus closing the shear head 18 and enabling movement of the tool 10, 110 within the test socket 82.

Figure 5:
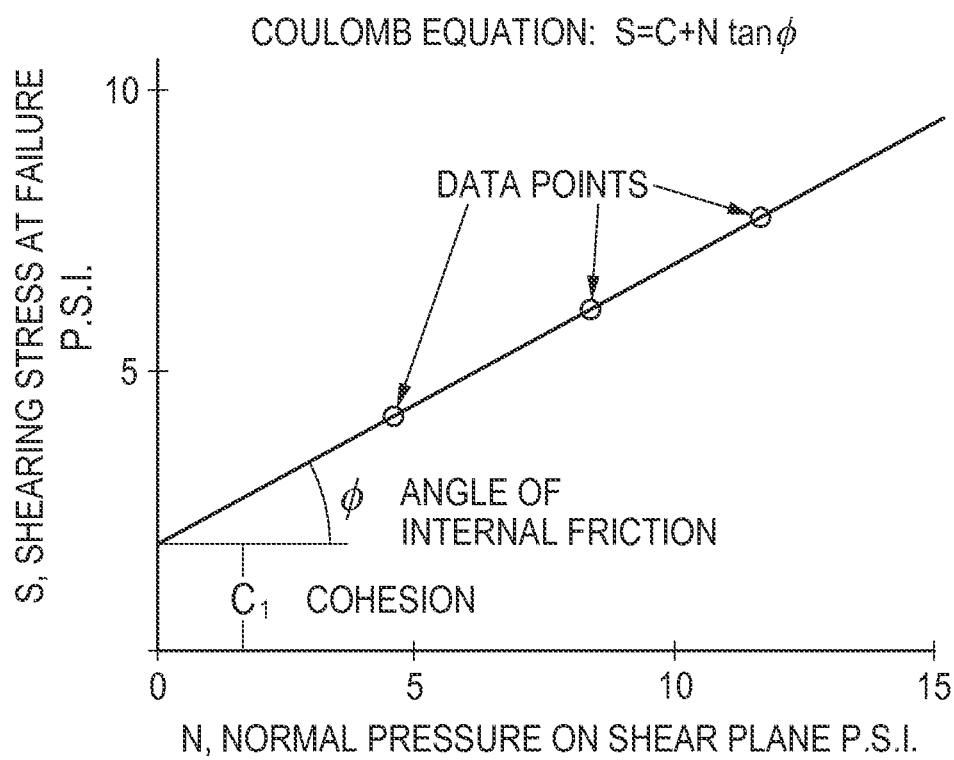
FIG. 5 is a graph of the Mohr-Coulomb failure envelope.

In this way, the shear head 18 can exert a normal force on the walls of the test socket 82, while the drill rod string 20, 120 provides the means for exerting an axial force on the same. This axial force induces shear failure in the rock of the test socket wall 82. These shear forces can be measured by a hydraulic load cell 36 located beneath shear plate 32, pistons 33, and piston heads 34, sending their response to surface via feedback lines 38. Normal forces induced by the shear head 18 can be measured via separate surface monitoring equipment and separate hydraulic lines. The shear force measurements provided by the shear head 18 provide multiple data points along the Mohr-Coulomb failure envelope, which provides both cohesion and internal friction values, illustrated by FIG. 5. The eight individual shear plates 32 may in this way be able to provide multiple data points along the Mohr-Coulomb failure envelope in one single test.

While the axial force on the shear head 18 can be provided by an upward movement of drill rod string 20, 120 shown in FIGS. 1 and 2, in some aspects the axial force may be supplied instead by a piston 235 supplying a force upward on the shear tester 218, as shown in FIG. 6. Pressure, power, and data transmission can be provided by an umbilical cable 250 comprising pneumatic and electrical lines running from the surface to the tool 10, 110. The umbilical cable 250 could comprise, for example, a logging cable braid. Power for the tools 10, 110, 210 can be provided from batteries 17 in the body 24, 124, 224. For example, a 15 volt 2 amp supply can be provided by 4 or more cylindrical batteries 17 disposed within the tool body 24, 124, 224. The umbilical cable 250 can act as a power line to keep the batteries 17 trickle-charged. A gas-charged reservoir 255 can be charged with pneumatic pressure supplied by the umbilical cable 250 and can connect to the cable 250, for example, via a 2-headed check valve that can control filling and venting of the reservoir 255. Such batteries 17 and reservoir 255 can allow the tool 10, 110, 210 to go deeper downhole and can in some aspects be capable of allowing the shear head 18, 218 to apply 30 MPa or more of force to the test socket 82 walls.

To operate the shear head 218 shown in FIG. 6, the membrane 215 can be inflated, causing the studs to move radially outward toward the walls of the test socket 82, and pushing the cones 227 into the walls of the socket 82. The shear head 218 can also comprise a limit switch that prevents overexpansion of the steel sheathing skin 217 beyond its elastic limits. In some aspects, the shear head 218 can apply more than 83 MPa of normal stress with a direct shear test and 100 MPa of shear stress. A piston 235 that can move in the axial direction can supply the shear force to the shear head 218. An axial movement detector can detect the point of material shear, and combined with the known co-ordinates of the normal and shear stress can allow the internal angle of friction and/or the cohesion to be determined.

The size of the physical contact points between the cones 227 and the surrounding test socket 82 wall can allow the area of force application to be determined, rather than relying on an assumption of known distance between two points or plates applying pressure.

Operation of the Micro-Frac Tester

In operation of the micro-frac tester 61 shown in FIGS. 1, 2, and 7a-7b, fluid is injected into the formation 26 through injection ports 63, which can be fluidly connected to the formation 26 through the opening of valves which are located within the tester 61 body. Pressure cells can be used to monitor pressure of the injection fluid in the tester 61 body. Such fluid injection can induce fracturing of the formation 26. Once fracture initiation is observed, the fluid injection can be terminated to allow the fracture to close. The fluid injection can then be re-started and pressure cells used to monitor the amount of force required to re-open the newly-created fracture.

Operation of the Heating Mechanism

After a baseline expansion test has been performed, a high temperature expansion test can take place using the heating mechanism shown in FIG. 2. The test socket 82 could be advanced to correspond to the length of the tool 110, for example, by approximately 1 meter, to allow accommodation space to raise and lower the tool 110 into the socket 82. The heating coils 28 could be activated, for example, by a separate electrical source at the surface via power cables 88. Once the formation 26 has been heated to the point that thermal hardening is believed to have occurred, which will be specific to the thermal diffusion properties of each specific formation, the heating coils 28 can deactivate and the tool 110 can be lowered to place the flexible membrane 15 in position adjacent to the heated area. The expansion test can then proceed as normal, creating a new dataset for the thermally hardened material.

In some aspects, advancing the test socket 82 only just prior to the heating process may be preferable in instances requiring running of multiple tests in the socket 82 at various zones of the formation 26, as this may avoid the need for hydraulic isolation during any injection processes being carried out in these tests. However, in other aspects, one could run a full suite of tests, drilling zone-by-zone during same (i.e. test, advance, test, advance, etc.), then come back uphole to carry out the high temperature tests only after the full suite of zone-by-zone tests in the downhole direction.

The use of at least two coils 28 in separate areas of the tool body 124 disposed adjacent and below the pressuremeter 114 can allow a testing process in which the heating coils 28 may be arranged for individual operation independently of one another. For example, one of the coils 28 may be disposed above the other, wherein the upper heating coil is run for a suitable time, and then the tool 110 can be lowered down the test socket 82 to situate the shear head 18 at the now-heated area of the socket 82 to perform a retest of the shear properties after thermal hardening of the formation material. Alternatively, a single heating coil may span upward through the pressuremeter 114 to the shear head 18. As yet another possibility, the tool may employ only a single heating coil at a location separate from the pressuremeter 114 and shear head 18, and rely on axial movement of the tool to move the selected tester (i.e. pressuremeter 114 or shear head 18) to the heated area of the formation 82 when the heating process is complete. In addition to such possibility of various heater locations relative to the pressuremeter 114 and shear head 18, it will be appreciated that the pressuremeter 114 need not necessarily be situated further downhole than the shear head 18 and accordingly, these testers 114, 18 may occupy different relative positions than those shown in the illustrated embodiments.

The expanding bladder provided by the flexible membrane 15 of the pressuremeters 14, 114, as well as the system of shear plates 32 or the system of studs 223 and cones 227, can permit the application of normal, lateral, and outward radial forces to a borehole wall or test socket 82. The shear plates 32 can be extended outward by the use of hydraulic fluid, the studs 223 and cones 227 can be extended outward by expansion of the membrane 215, and the bladder or flexible membrane 15 can be expanded by gas so as to exert the normal, lateral, and outward forces on the formation 82. As an axial force is exerted on the tools 10, 110, 210, shear failure can be caused in the formation 82 when the shear plates 32 or cones 227 are engaged with the socket 82 walls. In some aspects, the tools 10, 110, 210 have the capability to inject fluid into the target formation 82 at pressures of over 5,000 kPa. In some aspects, the expanding bladder 15 has the capability to exert over 20,000 kPa of force, as does the system of shear plates 32. In further aspects, the tools 10, 110 have the ability to drill their own test socket 82 by means of a rotating drill bit 12, 112 that is disposed inside the tool 10, 110, coupled with sharp cutting edges that cut into the rock formation 82 while the device 10, 110 drills. This can ensure the tightest tool fit possible in the drilled test socket 82, which can allow for the higher quality data as the flexible membrane 15 expands against the test socket 82 walls.

In some aspects, the tool 10, 110 can comprise other components, such as a hydraulic fracturing section that incorporates on/off valves within the test socket 82. Other components that could be included could be a compass 254, an inclinometer 252 and an external temperature measurement device 253.

The foregoing is considered as illustrative only of the principles of the invention. Further, since numerous changes and modifications will readily occur to those skilled in the art, it is not desired to limit the invention to the exact construction and operation shown and described, and accordingly, all such suitable changes or modifications in structure or operation which may be resorted to are intended to fall within the scope of the claimed invention.

The invention claimed is:

1. A shear tester for in-situ determination of rock formation geomechanical properties comprising:
    a radially expandable cylindrical membrane;
    a metal sheath covering at least a portion of the outer surface of the expandable membrane;
    at least one stud fixed on the outer surface of the sheath;
    at least one cone fixed on each of the at least one stud; and
    a piston operable to apply an upward axial force on the metal sheath.

2. The tester of claim 1, wherein the membrane is made out of continuous layers.

3. The tester of claim 1, and further comprising a biasing means to bias the membrane into a retracted position.

4. A device for in-situ determination of rock formation geomechanical properties comprising:
    a pressuremeter; and
    a shear tester comprising:
        a radially expandable cylindrical membrane;
        a metal sheath covering at least a portion of the outer surface of the expandable membrane;
        at least one stud fixed on the outer surface of the sheath;
        at least one cone fixed on each of the at least one stud; and
        a piston operable to apply an upward axial force on the metal sheath.

5. The device of claim 4, further comprising an umbilical cable comprising pneumatic and electrical lines running to the device from the surface of the rock formation.

6. The device of claim 5, further comprising a gas-charged reservoir and at least one trickle-charge battery, wherein the at least one trickle-charge battery is supplied power by the umbilical cable and the gas-charged reservoir is charged with pneumatic pressure supplied by the umbilical cable.

7. The device of claim 4, further comprising a heating mechanism for thermal hardening of a borehole wall in the formation.

8. The device of claim 7, further comprising a heat insulative barrier insulating the heating mechanism from other components of the device.

9. The device of claim 7, wherein the heating mechanism comprises at least one heating coil encircling an axial passage in the device.

10. The device of claim 7, wherein the heating mechanism comprises at least two heating coils in spaced relation axially along the device.

11. The device of claim 4, further comprising a mini-frac tester.

12. A method for in-situ determination of geomechanical properties of a rock formation comprising the steps of:
    providing a shear tester comprising
        an expandable membrane;
        a metal sheath covering at least a portion of the expandable membrane;
        at least one stud fixed on the surface of the sheath;
        at least one cone fixed on each of the at least one stud; and
        a piston operable to apply an upward axial force on the metal sheath;
    applying a normal force to the formation by expanding the membrane until at least one of the at least one cone penetrates the rock formation; and
    applying an upward axial force to the at least one of the at least one cone by operating the piston until at least a portion of the rock formation shears.

13. The method of claim 12 further comprising the steps of:
    providing an axial movement detector; and
    detecting the point of rock formation shear using the axial movement detector.

14. The method of claim 12 further comprising the step of providing an umbilical cable comprising at least one of a pneumatic line and an electrical line running from the surface of the rock formation.

15. The method of claim 14 further comprising the steps of:
    providing at least one trickle-charge battery; and
    supplying power to the trickle-charge battery from the umbilical cable.

16. The method of claim 14 further comprising the steps of:
    providing at least one gas-charged reservoir; and
    charging the at least one gas-charged reservoir with pneumatic pressure from the umbilical cable.

17. The method of claim 12 further comprising the step of heating at least a portion of the formation with a heating mechanism prior to the application of a normal force to the formation.

18. The method of claim 12 further comprising the step of operating a pressuremeter on the formation before or after the operation of the shear tester on the formation, without removal of the shear tester or pressuremeter from the formation between operation of the shear tester and pressuremeter.

19. The method of claim 12 further comprising the steps of:
    injecting high pressure fluid into the formation to initiate formation fracturing;
    terminating fluid injection;
    injecting high pressure fluid into the formation to re-initiate formation fracturing; and
    monitoring the force required to re-initiate formation fracturing.

* * * * *